United States Patent
Kato et al.

(10) Patent No.: US 7,091,389 B1
(45) Date of Patent: Aug. 15, 2006

(54) METHOD FOR PRODUCING AROMATIC COMPOUND ISOMERS

(75) Inventors: Masashi Kato, Nagoya (JP); Yasuharu Kato, Nagoya (JP); Koichi Okada, Nagoya (JP)

(73) Assignee: Toray Industries, Inc., (JP)

( * ) Notice: Subject to any disclaimer, the term of this patent is extended or adjusted under 35 U.S.C. 154(b) by 0 days.

(21) Appl. No.: 09/648,248

(22) Filed: Aug. 25, 2000

(30) Foreign Application Priority Data

Aug. 26, 1999 (JP) .............................. H11-240393

(51) Int. Cl.
*C07C 17/389* (2006.01)
*C07C 17/38* (2006.01)

(52) U.S. Cl. ...................... 570/211; 570/211

(58) Field of Classification Search ................ 570/211
See application file for complete search history.

(56) References Cited

U.S. PATENT DOCUMENTS 4,962,245 A * 10/1990 Kanai et al. ................. 570/211
4,996,380 A * 2/1991 McCulloch et al. ........ 570/211

FOREIGN PATENT DOCUMENTS

EP    0 412 215 A1    2/1991
EP    0 425 740 A1    5/1991

* cited by examiner

*Primary Examiner*—Elvis O. Price
(74) *Attorney, Agent, or Firm*—DLA Piper Rudnick Gray Cary US LLP (57) ABSTRACT

In a process of producing an aromatic compound isomer substituted with alkyl group(s) and/or halogen atom(s), through adsorptive separation by the use of a zeolite-containing adsorbent and a desorbent, the desorbent is, after having been processed for removing impurities from it, supplied to the adsorptive separation step. In the process, the absorbent used is prevented from being degraded, and its life is prolonged to efficiently separate an aromatic compound isomer mixture into individual isomers.

16 Claims, 7 Drawing Sheets

Fig. 7 Time-dependent Change of Adsorption Recovery

METHOD FOR PRODUCING AROMATIC COMPOUND ISOMERS

BACKGROUND OF THE INVENTION

1. Field of the Invention

The present invention relates to a method for producing aromatic compound isomers. More precisely, the invention relates to a method of adsorptive separation for producing intended aromatic compound isomers by the use of a zeolite-containing adsorbent and a desorbent.

2. Description of the Related Art

Aromatic compounds are useful for starting materials for synthetic products and for intermediates for medicines and agricultural chemicals. For obtaining a specific isomer of an aromatic compound, known is a method of adsorptive separation that comprises contacting an isomer mixture with a zeolite-containing adsorbent.

For example, Japanese Patent Publication No. 45457/1989 discloses a method of using an adsorbent of faujasite zeolite for adsorptive separation of 2,6-dichlorotoluene; Japanese Patent Laid-Open No. 330025/1992 discloses a method of using an adsorbent of faujasite zeolite that indispensably contains potassium and lead ions, for adsorptive separation of m-dichlorobenzene; and Japanese Patent Publication No. 46933/1992 discloses a process of isomerizing halogenobenzene derivatives, in which HCl formed in the step of isomerization is first removed through distillation or the like, and a specific isomer is thereafter separated from the isomer mixture through adsorptive separation by the use of a zeolite adsorbent.

Regarding heterocyclic compounds, Japanese Patent Laid-Open Nos. 143162/1997 and 251230/1998 and EP 173,440 disclose a method of using an adsorbent of faujasite zeolite for adsorptive separation of a compound having a pyridine ring structure.

In the process of adsorptive separation of aromatic compound isomers by the use of a zeolite-containing adsorbent, the adsorbent is degraded while used continuously. In the process, therefore, the adsorbent used must be exchanged for a fresh one in good time or must be regenerated, for example, by burning it. Accordingly, a technique for prolonging the life or the regeneration cycle of adsorbent, if possible, will produce great industrial merits.

In the process of the above-mentioned Japanese Patent Publication No. 46933/1992 for adsorptive separation of an aromatic compound isomer by the use of a zeolite adsorbent, the step of removing the side product, HCl from the isomer mixture prior to the next step of separating the intended isomer by the use of the adsorbent is for preventing the adsorbent used from being degraded. However, the process is still not enough for satisfactorily prolonging the life and the regeneration cycle of the adsorbent to the industrial level.

In ordinary adsorptive separation of aromatic compound isomers, the desorbent used is generally circulated and reused. In the line, however, the desorbent circulated for reuse is often contaminated with minor impurities having existed in the starting aromatic compound isomers and with other impurities having formed through decomposition or reaction of the aromatic compound isomers and/or the desorbent, as the impurities accumulate in the desorbent being used and circulated. As a result, the adsorbent being thus used in the line will be gradually degraded.

SUMMARY OF THE INVENTION

The object of the invention is to efficiently produce aromatic compound isomers through adsorptive separation by the use of a zeolite-containing adsorbent, for which the adsorbent used is prevented from being degraded and its life is prolonged.

To attain its object, the invention provides a method for producing an aromatic compound isomer substituted with alkyl group(s) and/or halogen atom(s), through adsorptive separation by the use of a zeolite-containing adsorbent and a desorbent, wherein the desorbent is, after having been processed for removing impurities from it, supplied to the adsorptive separation step.

Preferred embodiments of the method of the invention are as follows:

The aromatic compound has a benzene ring or heterocyclic ring structure;

The aromatic compound is ring-substituted with at least one halogen element;

The impurities in the desorbent are removed through any of distillation, desorption or adsorption to a solid adsorbent;

The impurities in the desorbent are removed by replacing a part of the used desorbent with an impurity-free fresh desorbent;

All or part of the desorbent to be supplied to the adsorptive separation step is first continuously or intermittently supplied to a step of removing impurities from it, and then supplied to the adsorptive separation step.

DESCRIPTION OF THE PREFERRED EMBODIMENTS

The aromatic compound to be subjected to adsorptive separation according to the invention is an aromatic compound substituted with alkyl group(s) and/or halogen atoms(s). The aromatic compound includes a plurality of isomers. In cases where the boiling point difference between these isomers is small, the isomers are difficult to separate from each other through distillation. For the isomers, therefore, suitable is a method of separating them through adsorptive separation.

The aromatic compound substituted with alkyl group(s) and/or halogen atom(s) to be processed according to the invention shall have at least one substituent of alkyl groups or halogen atoms, but may optionally have, in addition to it, any other substituent(s), for example, oxygen-containing substituents such as hydroxyl groups, aldehyde groups, carboxyl groups, etc., and nitrogen-containing substituents such as —NO₂, —NH₂, —NHR, —NR₂, —NRR' (where R and R' are at least one of methyl, ethyl and propyl groups), etc.

The aromatic compound referred to herein is not limited to benzene derivatives only, but includes any others, for example, polycyclic aromatic compounds such as naphthalene, anthracene and phenanthrene compounds, etc., heterocyclic compounds such as pyridine and triazine compounds, etc.

Specific examples of the heterocyclic compounds are α-picoline, β-picoline, γ-picoline, 3,5-lutidine, 2,6-lutidine, 2,4-lutidine, 2,5-lutidine, 3,4-lutidine, 2,3-lutidine, 2,4,6-collidine, 2-ethylpyridine, 3-ethylpyridine, 4-ethylpyridine, 2-vinylpyridine, 3-vinylpyridine, 4-vinylpyridine, 2-pyridinemethanol, 3-pyridinemethanol, 4-pyridinemethanol, 2-aminopyridine, 3-aminopyridine, 4-aminopyridine, 2-dimethylaminopyridine, 3-dimethylaminopyridine, 4-dimethylaminopyridine, 2-aldehydopyridine, 3-aldehydopyridine, 4-aldehydopyridine, nicotinic acid, isonicotinic acid, picolinic acid, 2-chloropyridine, 3-chloropyridine, 4-chloropyridine, 3,5-dichloropyridine, 2,6-dichloropyridine, 2,4-dichloropyridine, 2,5-dichloropyridine, 3,4-dichloropyridine, 2,3-dichloropyridine, 2-cyanopyridine, 3-cyanopyridine, 4-cyanopyridine, 2-chloro-5-methylpyridine, 2-chloro-4-methylpyridine, 2-chloro-3-methylpyridine, 2-chloro-6-methylpyridine, methylpyrrole, ethylpyrrole, propylpyrrole, dimethylpyrrole, chloropyrrole, methylfuran, ethylfuran, propylfuran, dimethylfuran, chlorofuran, methylthiophene, ethylthiophene, propylthiophene, dimethylthiophene, chlorothiophene, methylquinoline, ethylquinoline, propylquinoline, dimethylquinoline, chloroquinoline, etc.

For the method of the invention, preferred are aromatic compounds substituted with alkyl group(s) and/or halogen atom(s) of the following general formula (I):

(I)

wherein R1 and R2 each represent any of halogen atoms or alkyl groups; and X1 and X2 each represent any of halogen atoms, hydrogen atoms or alkyl groups.

More preferred are those that are ring-substituted with at least one halogen element. Especially preferably, the halogen element is chlorine or bromine element. Even more preferred are aromatic compounds that are ring-substituted with chlorine atom(s).

Specific examples of the aromatic compounds (isomers) of formula (I) include xylene, trimethylbenzene, tetramethylbenzene, ethyltoluene, diethylbenzene, triethylbenzene, chlorotoluene, dichlorotoluene, trichlorotoluene, chloroethylbenzene, dichlorobenzene, trichlorobenzene, tetrachlorobenzene, bromotoluene, bromoethylbenzene, dibromobenzene, dibromotoluene, chlorobromobenzene, dibromochlorobenzene, dichlorobenzene, etc. Of those, the method of the invention is especially favorable to the production of chlorotoluene, dichlorotoluene, chloroethylbenzene, dichlorobenzene and trichlorobenzene.

In the invention, a zeolite-containing adsorbent is used for adsorptive separation of aromatic compound isomers such as those mentioned above.

Zeolite for use herein is not limited to crystalline aluminosilicates only, but includes any others, for example, crystalline aluminophosphates and silicoaluminophosphates such as ALPO, SAPO, etc.

The adsorbent shall be suitably selected, depending on the type of the compound to be separated with it. For example, for adsorptive separation of xylene, preferred is faujasite zeolite or the like; but for adsorptive separation of halogenoaromatic compounds such as chloroaromatic compounds, preferred is faujasite zeolite, pentasil zeolite or the like. These zeolite-containing adsorbents may be ion-exchanged with alkali metal salts, alkaline earth metal salts or the like for controlling their adsorption selectivity. For facilitating their use on an industrial scale, the adsorbents are preferably shaped along with a binder such as alumina, bentonite, etc.

The desorbent for use in the invention is not specifically defined. It includes, for example, aromatic compounds such as toluene, xylene, naphthalene, chlorobenzene, dichlorotoluene, etc. For separating heterocyclic compounds according to the invention, further usable are, in addition to the above-mentioned desorbents, any of aniline, methylaniline, dimethylaniline, diphenylamine, triphenylamine, toluidine, anisidine, chloroaniline, bromoaniline, nitroaniline, dinitroaniline, trinitroaniline, phenylenediamine, methylamine, dimethylamine, ethylamine, triethylamine, n-propylamine, di-n-propylamine, tri-n-propylamine, isopropylamine, n-butylamine, isobutylamine, sec-butylamine, tert-butylamine, cyclohexylamine, benzylamine, α-phenylethylamine, β-phenylethylamine, ethylenediamine, tetramethylenediamine, hexamethylenediamine, piperazine, piperidine, pyrrolidine, etc.

In the invention, it is important to remove impurities that may be in the desorbent and will degrade the adsorbent being used, from the desorbent. Preferably, the impurity content of the desorbent to be circulated and reused in the invention is as small as possible. Concretely, it is desirable that the impurity content is at most 1000 ppm by weight, more preferably at most 100 ppm by weight. Removing impurities from the desorbent is effective for preventing the desorbent being used from being degraded and for ensuring efficient adsorptive separation of aromatic compound isomers.

The method of measuring the impurities in the desorbent varies, depending on the type of the impurities. For example, the impurities therein may be measured through gas chromatography, Karl Fischer's moistometry, Beckman's dissolved oxygen analysis, colorimetry under heat, etc.

For removing the impurities from it, for example, the desorbent is processed through distillation, desorption, or adsorption to a solid adsorbent, or a part of the used desorbent is replaced with an impurity-free fresh desorbent.

Concretely, the desorbent that contains impurities is distilled to remove from it the impurities having a lower boiling point and/or the impurities having a higher boiling point through evaporation. The distillation may be effected in any ordinary manner. For example, the distillation tower to be used may be any of a plate column tower, a packed tower, etc., and the condition for operating it is not specifically defined.

For removing the impurities from the desorbent through desorption, for example, employable is any of a method of directly bubbling N₂ into the desorbent in a storage tank, or a method of contacting the desorbent with N₂ in countercurrent streams of the two in a plate column tower, a packed tower, a packed tower, etc. The condition for the methods is not specifically defined.

The desorbent may be processed through adsorption to a solid adsorbent for removing impurities from it. For example, the desorbent that contains impurities is contacted with a solid adsorbent so that the impurities are selectively adsorbed by the solid adsorbent, whereby the impurities are removed from the desorbent. For contacting the desorbent with a solid adsorbent, employable is any of a fixed bed, a fluidized bed, etc. The solid adsorbent includes, for example, activated charcoal, zeolite, acid clay, activated clay, alumina, etc.

Of the impurities that may accumulate in the desorbent used in the process of adsorptive separation, highly polar substances such as water, hydrochloric acid, phenols and others strongly adsorb onto the surface of the adsorbent to lower the adsorptive separation capability of the adsorbent. Of those, dimers of aromatic compounds will be carbonated in the adsorbent to thereby also lower the adsorptive separation capability of the adsorbent. Therefore, removing these impurities from the desorbent, if possible, will be effective for preventing the adsorbent from being degraded, whereby the regeneration cycle of the adsorbent could be prolonged. Accordingly, in the invention, it is desirable to remove the impurities of water, hydrochloric acid, phenols, dimers of aromatic compounds, unsaturated hydrocarbon-containing compounds, and also oxygen-containing compounds such as those having aldehyde groups, carboxyl groups and the like, from the desorbent.

In the method of the invention, all or part of the desorbent to be circulated and reused in the adsorptive separation step may be processed in the previous step of removing the impurities from it, and it may be supplied to the impurities removing step either continuously or intermittently.

In the method of the invention, the adsorptive separation may be effected in any known manner. For example, it may be effected in any of a fixed bed, a fluidized bed or a moving bed, in any manner of a flow process or batch process. The isomer mixture and the desorbent to be processed for such adsorptive separation may be in a vapor phase or a liquid phase. One typical process for adsorptive separation is a simulated moving bed process.

EXAMPLES

The invention is described concretely with reference to the following Examples, which, however, are not intended to restrict the scope of the invention.

Example 1

Figure 1:
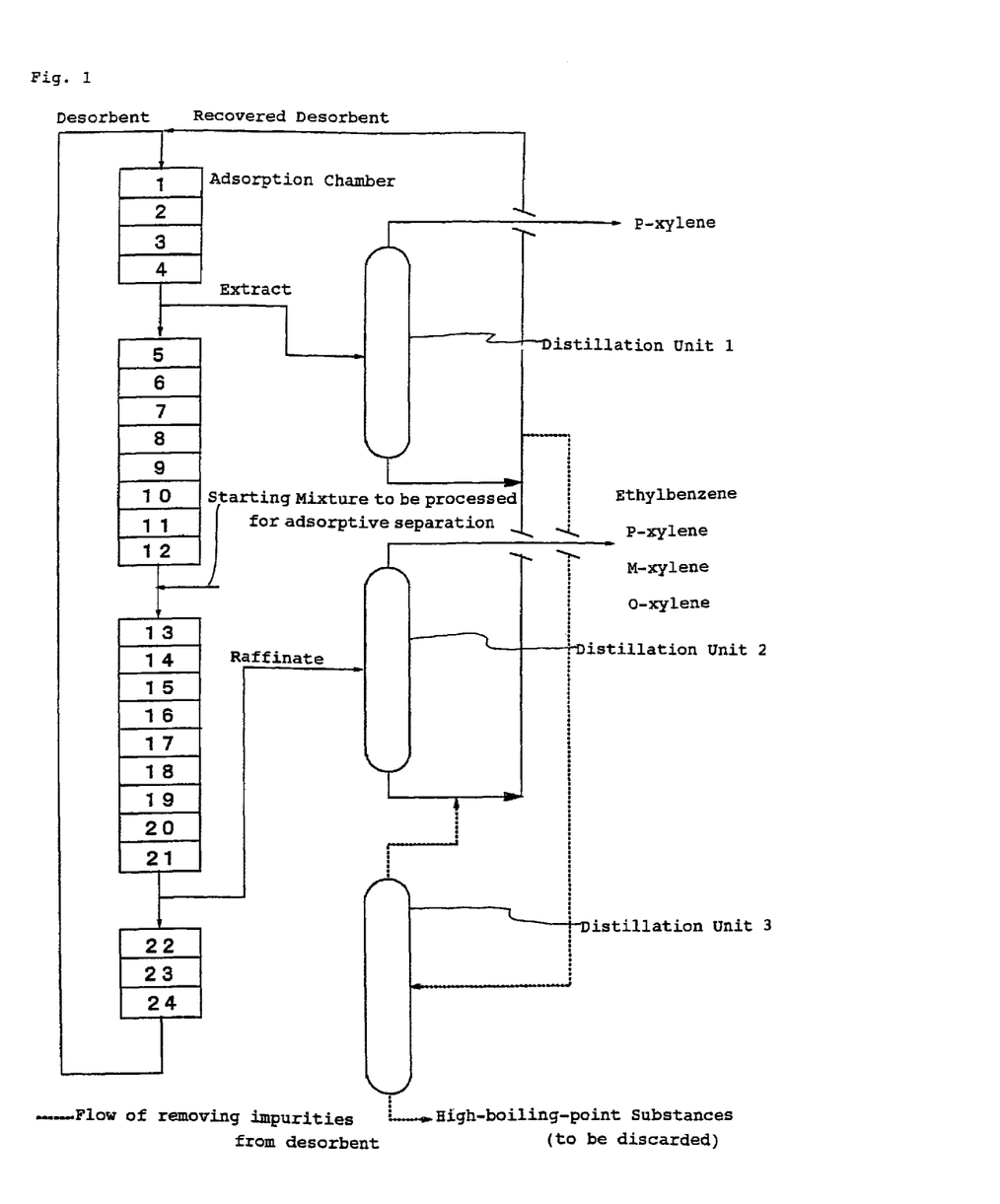
FIG. 1 is a flow chart for removing impurities from the desorbent in the simulated moving bed process of Example 1.

Na—Y type zeolite having a molar ratio $SiO_2/Al_2O_3$ of 4.8 (from Shokubai Kasei) is prepared according to the method described in the section of Examples in Japanese Patent Laid-Open No. 15833/1973, and ion-exchanged into an adsorbent of K-Y type zeolite. Using this, paraxylene (hereinafter referred to as PX) is separated from a mixture essentially comprising xylene isomers and ethylbenzene (this is a starting mixture to be subjected to adsorptive separation herein, and is hereinafter referred to as a starting mixture). For the system to be used herein, the simulated moving bed system described in Example 5 in Japanese Patent Laid-Open No. 330025/1992 is so modified that it has 24 adsorption chambers. The outline of the system used herein is shown in FIG. 1; the condition for adsorptive separation in the system is in Table 1; and the composition of the starting mixture is in Table 2. In this system, used is at least 90 wt. % paradiethylbenzene (hereinafter referred to as p-DEB) as the desorbent, and the starting mixture is subjected to adsorptive separation. The intended product, PX is taken out as an extract flow along with the desorbent; and the remaining PX not having been recovered in the extract flow and the other components of the starting mixture are taken out as a raffinate flow along with the desorbent. The extract and the raffinate are then processed in the distillation units 1 and 2, respectively, to recover the desorbent. The thus-recovered desorbent is circulated and reused in the system along with the desorbent also recovered from the 24th adsorption chamber. When contacted with the adsorbent at high temperatures in the system, the starting mixture and the desorbent will form high-boiling-point substances such as dimers, etc.; or when contacted with minor $O_2$ in the $N_2$ streams in the distillation units, they will form oxygen-containing compounds having an aldehyde group or a carboxyl group. Though their amount is small, these impurities will accumulate in the desorbent to be circulated and reused in the system whereby the adsorptive separation capability of the system is lowered.

As an index of the separation capability of the system, employed is the "adsorption recovery" for 99.80 wt. % product purity to be defined by the following equation, and its time-dependent change is plotted, based on the adsorption recovery at the start of the system.

Adsorption Recovery=[(amount of PX recovered as product, g/hr)/(amount of PX in Xylene isomer mixture processed for adsorptive separation, g/hr)]×100

Figure 2:
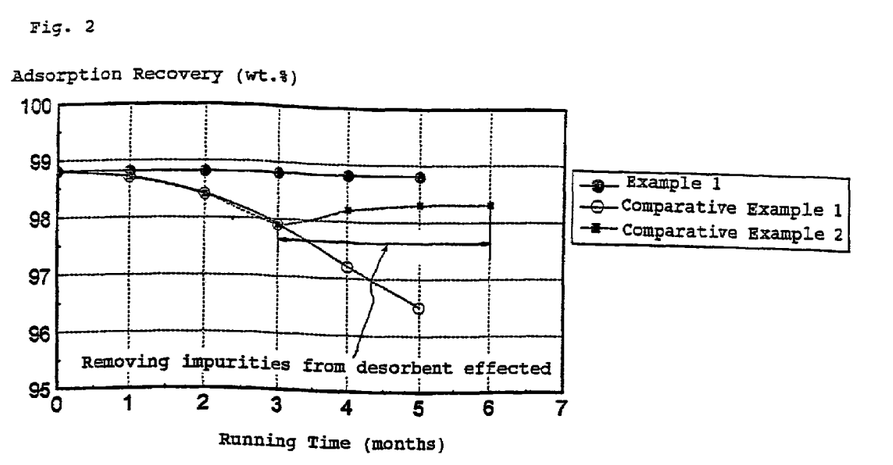
FIG. 2 is a graph of adsorption recovery versus running time in Example 1 and Comparative Examples 1 and 2.
Figure 3:
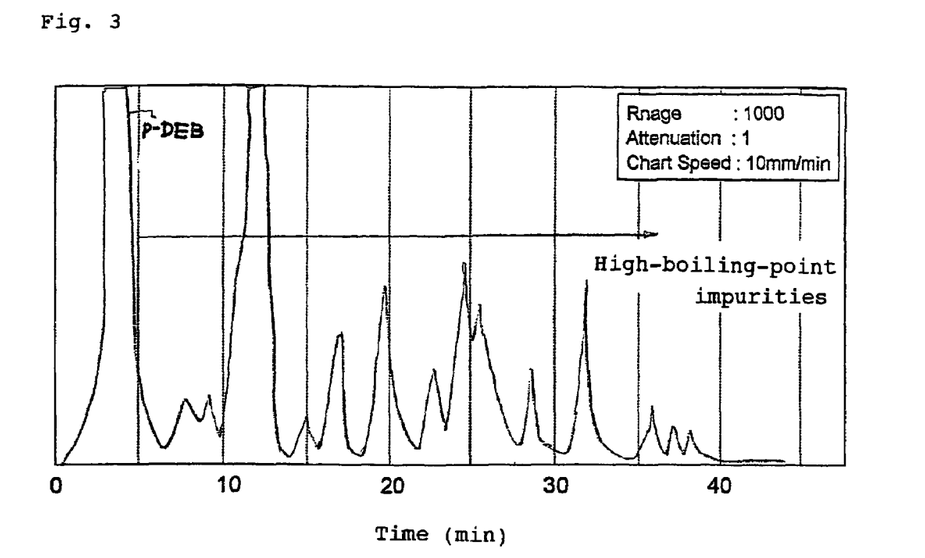
FIG. 3 is a chart of high-boiling-point impurities accumulated in the desorbent in Example 1.

In this Example, a part of the desorbent is continuously extracted out and processed in the distillation unit 3 to remove the high-boiling-point substances from it, and then circulated and reused in the system. Accordingly, the adsorption capability of the system is not lowered as in FIG. 2. On the other hand, the high-boiling-point substances having been removed from the desorbent are concentrated and analyzed through gas chromatography, for which the condition is shown in Table 3. From the chart of the gas chromatogram shown in FIG. 3, it is seen that many high-boiling-point substances are in the desorbent.

Comparative Example 1

The same absorptive separation process as in Example 1 is repeated herein. In this, however, the step of continuously extracting a part of the desorbent to be circulated and reused in the system, and processing it for removing impurities therefrom through distillation is omitted. The adsorption recovery in the system is greatly lowered, as in FIG. 2.

Comparative Example 2

First, the adsorptive separation process of Comparative Example 1 is repeated for a while, but in the halfway through it, this is combined with the step of desorbent purification as in Example 1. In this, the adsorptive recovery in the system is greatly lowered before the halfway, but the reduction in the adsorptive recovery is stopped after the start of the step of removing impurities, as in FIG. 2.

Example 2

Figure 4:
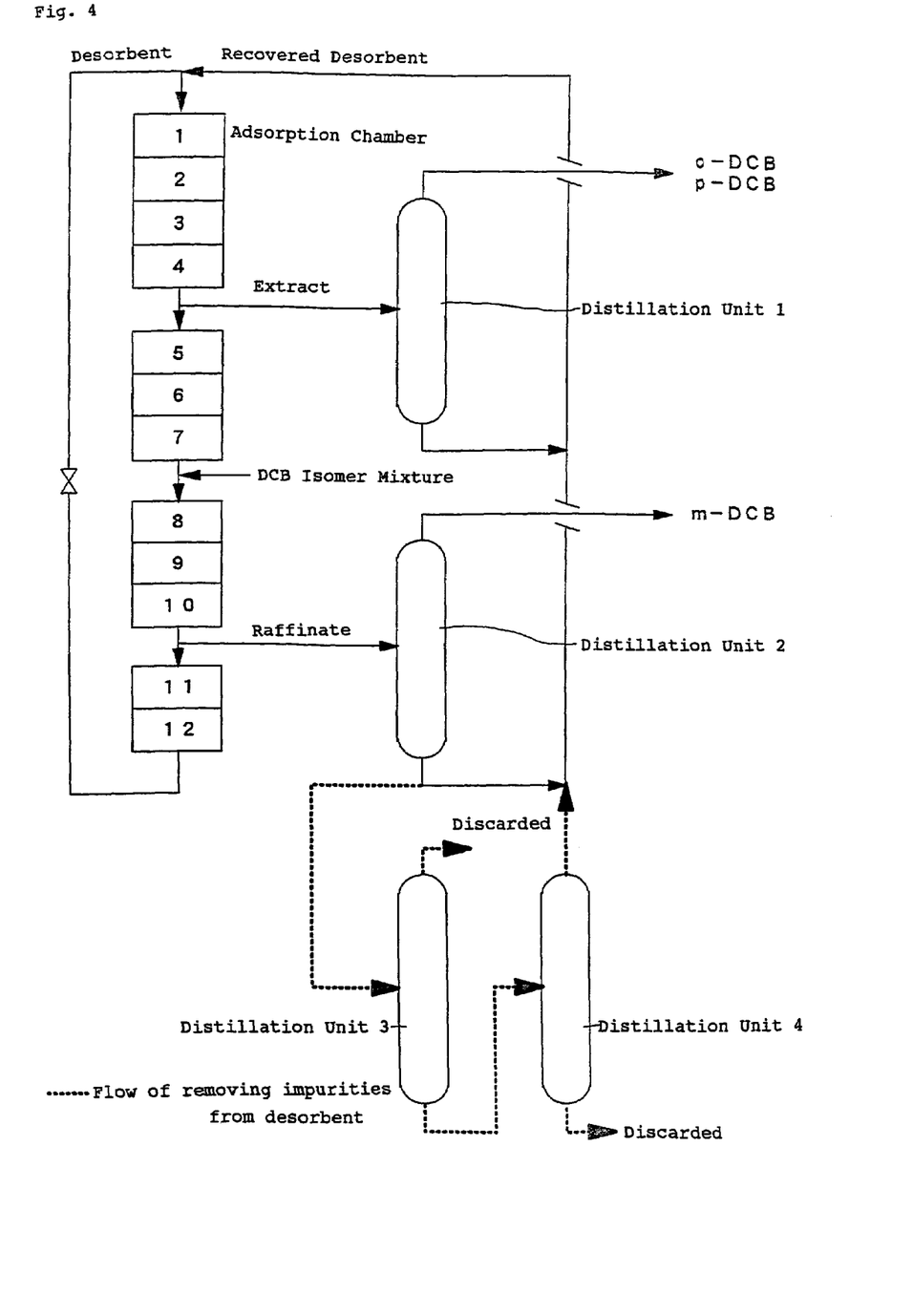
FIG. 4 is a flow chart for removing impurities from the desorbent in the simulated moving bed process of Example 2.

A zeolite adsorbent for separation of m-dichlorobenzene (hereinafter referred to as m-DCB) is prepared according to the method described in Examples 1 to 4 in Japanese Patent Laid-Open No. 330025/1992. This is Y-type zeolite containing cations of potassium and lead ions. The adsorbent is baked at 500° C. for 2 hours, and set in a simulated moving bed system for adsorptive separation, as in Example 5 in Japanese Patent Laid-Open No. 330025/1992. The outline of the system used herein is shown in FIG. 4; and the condition for adsorptive separation in the system is in Table 4. In this system, used is 3,4-dichlorotoluene (hereinafter referred to as 3,4-DCT) is used as the desorbent, and a DCB isomer mixture is subjected to adsorptive separation. The intended product, m-DCB is taken out as a raffinate flow along with the desorbent; and the remaining m-DCB not having been recovered in the raffinate flow and the other components o-DCB and p-DCB are taken out as an extract flow along with the desorbent. The extract and the raffinate are then processed in the distillation units 1 and 2, respectively, to recover the desorbent. The thus-recovered desorbent is circulated and reused in the system along with the desorbent also recovered from the adsorption chamber 12. When heated, 3,4-DCT forms a small amount of high-boiling-point substances such as biphenylmethanes, etc. The impurities generally accumulate in the desorbent to be circulated and reused in the system whereby the adsorptive separation capability of the system is lowered.

As an index of the separation capability of the system, employed is the adsorption recovery for 99.5% product purity to be defined by the following equation, and its time-dependent change is plotted, based on the adsorption recovery at the start of the system.

> Adsorption Recovery=[(amount of m-DCB recovered as product, g/hr)/(amount of m-DCB in DCB isomer mixture processed for adsorptive separation, g/hr)]×100

Figure 5:
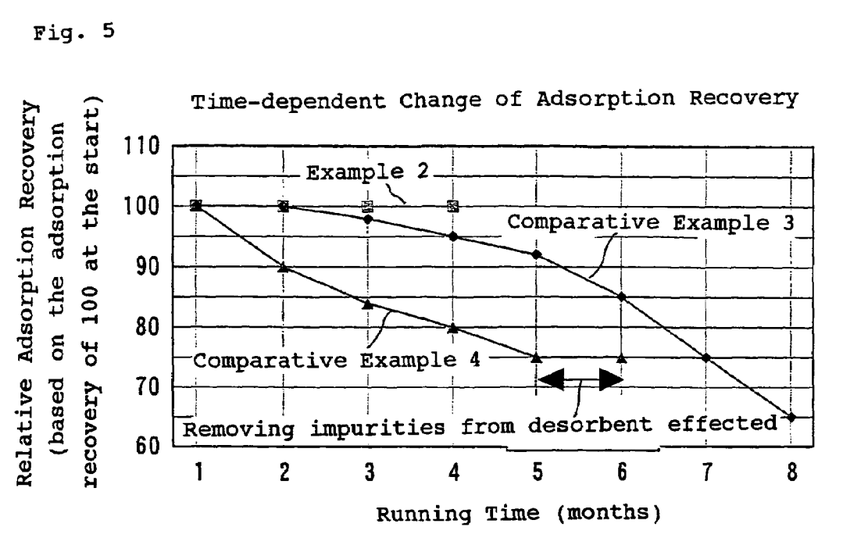
FIG. 5 is a graph of adsorption recovery versus running time in Example 2 and Comparative Examples 3 and 4.
Figure 6:
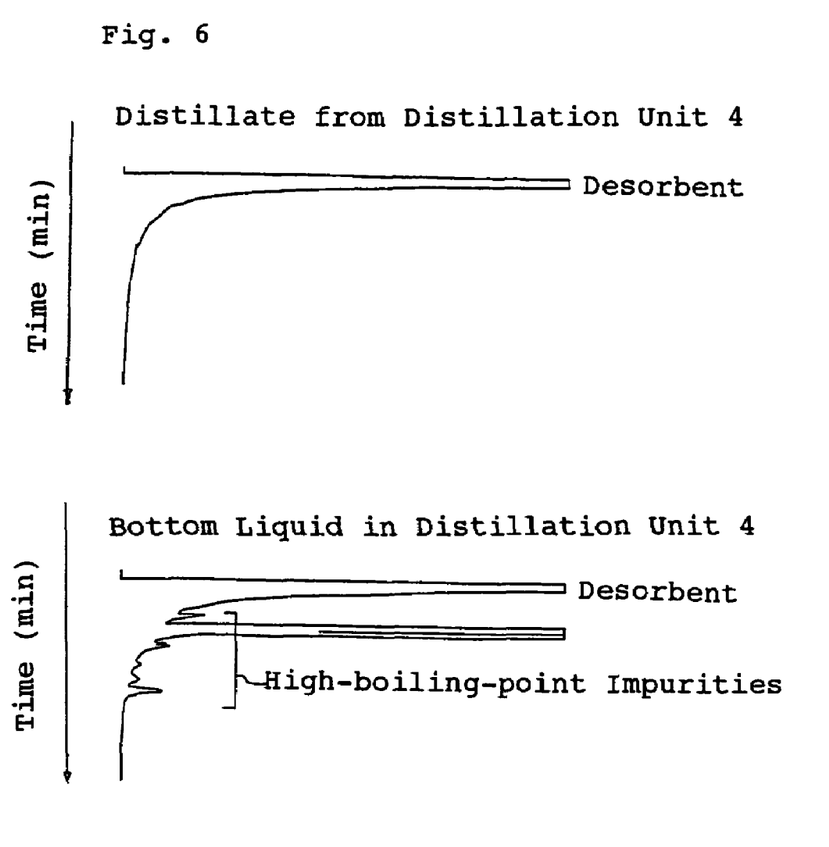
FIG. 6 is a chart of high-boiling-point impurities in the distillate from the distillation unit and the bottom liquid remained in the unit in Example 2.

In this Example, a part of the desorbent is continuously extracted out and processed in the distillation units 3 and 4 to remove the impurities from it, and then circulated and reused in the system. Accordingly, the adsorption capability of the system is not lowered as in FIG. 5. On the other hand, the high-boiling-point substances having been removed from the desorbent are concentrated and analyzed through gas chromatography, for which the condition is shown in Table 5. From the chart of the gas chromatogram shown in FIG. 6, it is seen that many high-boiling-point substances are in the desorbent.

TABLE 1

| Item | Condition |
|---|---|
| Adsorption Chambers | 16 ml × 24 chambers |
| Amount of Desorbent fed into system | 138.7 gr/hr |
| Amount of Starting Mixture fed into system | 62.7 gr/hr |
| Amount of Extract Flow | 61.6 gr/hr |
| Amount of Raffinate Flow | 139.8 gr/hr |
| Adsorption Temperature | 175° C. |
| Amount of Desorbent Flow Circulated and Reused after Distillation | 1.6 gr/hr |

TABLE 2

| Component | Concentration |
|---|---|
| Ethylbenzene | 7.68 wt.% |
| Paraxylene | 21.23 wt.% |
| Metaxylene | 49.19 wt.% |
| Orthoxylene | 21.90 wt.% |

TABLE 3

| Item | Condition |
|---|---|
| Detector | FID |
| Column | Thermol-3 (5%), Celite 545 |
| Column Temperature | 100° C. → 240° C. (programmed temperature gas chromatography) |
| Inlet Port Temperature | 250° C. |
| Heating Rate | 8° C./min |
| Time at which heating started | 240 seconds after sample introduction |
| Carrier Gas | N2, 30 cc/min |
| Amount of Sample applied to column | 1 μl |

TABLE 4

| Item | Condition |
|---|---|
| Capacity of Adsorption Chambers | 16 ml × 12 chambers |
| Amount of Desorbent fed into system | 364 ml/hr |
| Amount of DCB Isomer Mixture fed into system | 16 ml/hr |
| Amount of Extract Flow | 71 ml/hr |
| Amount of Raffinate Flow | 37 ml/hr |
| Adsorption Temperature | 130° C. |
| Time for switching simulated moving beds | about 150 seconds |
| Amount of Desorbent Flow Circulated and Reused after Distillation | 12 ml/hr |

TABLE 5

| Item | Condition |
|---|---|
| Detector | FID |
| Column | Silicon OV-17 (5%)/Uniport B, 60–80 mesh, 2 m × 3 mmφ |
| Column Temperature | 250° C. |
| Inlet Port Temperature | 300° C. |
| Carrier Gas | N2, 225 kPa |
| Air | 50 kPa |
| Hydrogen | 60 kPa |
| Amount of Sample applied to column | 1 μl |

Comparative Example 3

The same absorptive separation process as in Example 2 is repeated herein. In this, however, the step of continuously extracting a part of the desorbent to be circulated and reused in the system, and processing it for removing impurities therefrom through distillation is omitted. The adsorption recovery in the system is greatly lowered, as in FIG. 5.

Comparative Example 4

First, the adsorptive separation process of Comparative Example 1 is repeated for a while, but in the halfway through it, this is combined with the step of desorbent purification as in Example 2. In this, the adsorptive recovery in the system is greatly lowered before the halfway, but the reduction in the adsorptive recovery is stopped after the start of the step of removing impurities, as in FIG. 5.

Example 3

To 100 parts by weight of sodium-type Y-type zeolite (hereinafter referred to as Na—Y) (powdered product of Zeolum Na-5.1Y from Toso), added is 15 parts by weight, in terms of alumina, of alumina sol (Nissan Chemical's Alumina Sol #200 with $Al_2O_3$=10 wt. %) serving as a binder, and granulated into 0.15 to 0.5 mm φ granules. The NaY-type zeolite granules are dried at 120° C., and then baked at 500° C. for 2 hours. With an aqueous solution of silver nitrate that corresponds to 50% (in terms of the metal by mol) of the Na cation site of Na—Y, the zeolite granules are ion-exchanged (solid/liquid ratio, 3.0 liters/kg) by keeping them therein at room temperature for 30 minutes and then heating them at 85° C. for 1 hour. These are then fully washed with distilled water, dried at 120° C., and then baked at 500° C. for 2 hours.

Using the adsorbent (Ag—Na—Y) together with 2,4-xylidine serving as a desorbent, a mixture of α-picoline:β-picoline:2,6-lutidine:2,4-lutidine=1:1:1:1 (by weight) is processed for adsorptive separation in the same manner as in Example 2.

The intended product, 2,6-lutidine is taken out as a raffinate flow along with the desorbent; and the remaining 2,6-lutidine not having been recovered in the raffinate flow and the other components α-picoline, β-picoline and 2,4-lutidine are taken out as an extract flow along with the desorbent.

As an index of the separation capability of the system, employed is the adsorption recovery for 99.5% product purity to be defined by the following equation, and its time-dependent change is plotted, based on the adsorption recovery at the start of the system.

Adsorption Recovery=[(amount of 2,6-lutidine recovered as product, g/hr)/(amount of 2,6-lutidine in substituted pyridine mixture processed for adsorptive separation, g/hr)]×100

Figure 7:
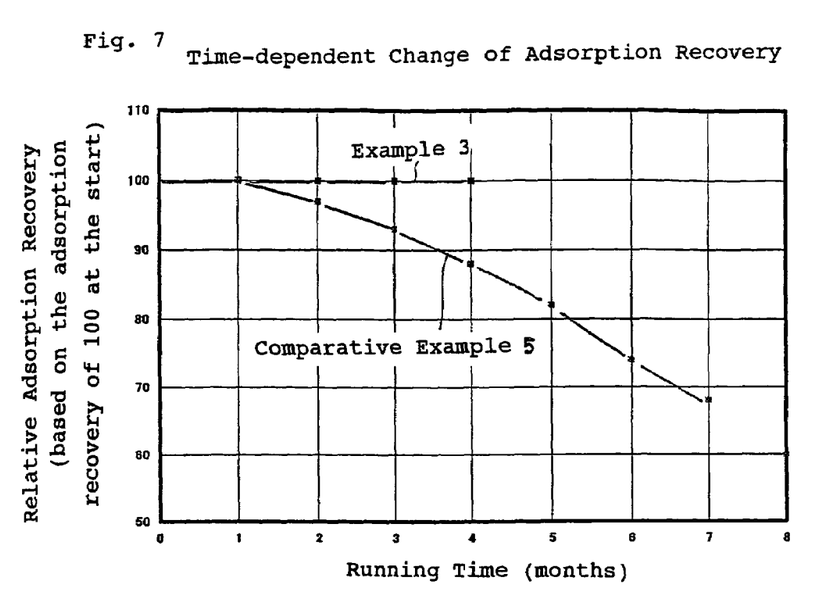
FIG. 7 is a graph of adsorption recovery versus running time in Example 3 and Comparative Example 5.

In this Example, a part of the desorbent is continuously extracted out and processed in the distillation units 3 and 4 to remove the impurities from it, and then circulated and reused in the system. Accordingly, the adsorption capability of the system is not lowered as in FIG. 7.

Comparative Example 5

The same absorptive separation process as in Example 3 is repeated herein. In this, however, the step of continuously extracting a part of the desorbent to be circulated and reused in the system, and processing it for removing impurities therefrom through distillation is omitted. The adsorption recovery in the system is greatly lowered, as in FIG. 7.

While the invention has been described in detail and with reference to specific embodiments thereof, it will be apparent to one skilled in the art that various changes and modifications can be made therein without departing from the spirit and scope thereof.

What is claimed is:

1. A method for separating an aromatic compound isomer substituted with alkyl group(s) and/or halogen atom(s) comprising subjecting a starting mixture containing the aromatic compound isomer to adsorptive separation by the use of a zeolite-containing adsorbent and a desorbent, subjecting the desorbent, after it has been collected from the adsorptive separation, to a method selected from the group consisting of distillation, purging, and adsorption to a solid adsorbent to achieve a level of impurities below 1,000 ppm by weight, the impurities being selected from the group consisting of water, hydrochloric acid, phenols, dimers of aromatic compounds, unsaturated hydrocarbon-containing compounds and oxygen-containing compounds, and after having been processed to remove impurities, supplying the desorbent to the adsorptive separation step and collecting the separated aromatic compound isomer.

2. The method for producing an aromatic compound isomer as claimed in claim 1, wherein the aromatic compound has a benzene ring or heterocyclic ring structure.

3. The method for producing an aromatic compound isomer as claimed in claim 1 or 2, wherein the aromatic compound is ring-substituted with at least one halogen element.

4. The method for producing an aromatic compound isomer as claimed in claim 1, wherein the impurities in the desorbent are removed by replacing a part of the used desorbent with an impurity-free fresh desorbent.

5. The method for producing an aromatic compound isomer as claimed in claim 1, wherein all or part of the desorbent to be supplied to the adsorptive separation step is first continuously or intermittently supplied to a step of removing impurities from it, and then supplied to the adsorptive separation step.

6. A method for separating an aromatic compound isomer substituted with alkyl group(s) and/or halogen atom(s) comprising subjecting a starting mixture containing the aromatic compound isomer to adsorptive separation by the use of a zeolite-containing adsorbent and a desorbent, subjecting the desorbent, after it has been collected from the adsorptive separation, to a method selected from the group consisting of distillation, purging, and adsorption to a solid adsorbent to achieve a level of impurities below 1,000 ppm by weight, the impurities being oxygen-containing or high boiling point compounds, and after having been processed to remove impurities, supplying the desorbent to the adsorptive separation step and collecting the separated aromatic compound isomer.

7. A method for separating an aromatic compound isomer substituted with alkyl group(s) and/or halogen atom(s) comprising subjecting a starting mixture containing the aromatic compound isomer to adsorptive separation by the use of a zeolite-containing adsorbent and a desorbent, subjecting the desorbent, after it has been collected from the adsorptive separation, to a method selected from the group consisting of distillation, purging, and adsorption to a solid adsorbent to achieve a level of impurities below 1,000 ppm by weight, the impurities having an aldehyde group or a carboxyl group, and after having been processed to remove impurities, supplying the desorbent to the adsorptive separation step and collecting the separated aromatic compound isomer.

8. A method for separating an aromatic compound isomer substituted with alkyl group(s) and/or halogen atom(s) comprising subjecting a starting mixture containing the aromatic compound isomer to adsorptive separation by the use of a zeolite-containing adsorbent and a desorbent, subjecting the desorbent, after it has been collected from the adsorptive separation, to a method selected from the group consisting of distillation, purging, and adsorption to a solid adsorbent to achieve a level of impurities below 1,000 ppm by weight, the impurities having been produced during adsorptive separation, and after having been processed to remove impurities, supplying the desorbent to the adsorptive separation step and collecting the separated aromatic compound isomer.

9. A method for separating an aromatic compound isomer substituted with alkyl group(s) and/or halogen atom(s) comprising subjecting a starting mixture containing the aromatic compound isomer to adsorptive separation by the use of a zeolite-containing adsorbent and a desorbent, subjecting the desorbent, after it has been collected from the adsorptive separation, to a method selected from the group consisting of distillation, purging, and adsorption to a solid adsorbent to achieve a level of impurities below 1,000 ppm by weight, the impurities having been produced during adsorptive separation and being selected from the group consisting of oxygen-containing or high boiling point compounds and compounds having an adehyde group or a carboxyl group, and after having been processed to remove impurities, supplying the desorbent to the adsorptive separation step and collecting the separated aromatic compound isomer.

10. A method of producing a composition comprising an aromatic isomer substituted with alkyl group(s) and/or halogen atom(s), the method comprising:
(a) subjecting a starting mixture containing aromatic isomer to adsorptive separation by the use of a zeolite-containing adsorbent and a desorbent, the adsorptive separation producing impurities;
(b) withdrawing a fluid from the adsorptive separation, the fluid comprising desorbent and at least a portion of said aromatic isomer;
(c) separating the desorbent from said aromatic isomer;
(d) collecting said aromatic isomer to form the composition;
(e) removing impurities from the desorbent to achieve an impurity level below 1,000 ppm by weight; and
(f) after removing impurities, supplying the desorbent to the adsorptive separation step.

11. The method of claim 10 wherein the fluid is extract.

12. The method of claim 11 further comprising the steps of
withdrawing a raffinate from the adsorptive separation, the raffinate comprising a second portion of desorbent, a second portion of said aromatic isomer and at least one other isomer;
separating the second portion of the desorbent from the second portion of said aromatic isomer and other isomer;
removing impurities from the second portion of the desorbent to achieve an impurity level below 1,000 ppm by weight;
after removing impurities, supplying the second portion of the desorbent to the adsorptive separation step.

13. The method of claim 10 wherein the fluid is raffinate.

14. The method of claim 13 further comprising the steps of
withdrawing an extract from the adsorptive separation, the extract comprising a second portion of desorbent, a second portion of said aromatic isomer and at least one other isomer;
separating the second portion of the desorbent from the second portion of said aromatic isomer and other isomer;
removing impurities from the second portion of the desorbent to achieve an impurity level below 1,000 ppm by weight;
after removing impurities, supplying the second portion of the desorbent to the adsorptive separation step.

15. The method of claim 10 wherein the step of removing impurities comprises a method selected from the group consisting of distillation, purging, and adsorption to a solid adsorbent.

16. The method of claim 10 wherein the impurities produced during the adsorptive separation are oxygen-containing compounds, high boiling point compounds, compounds having an adehyde group or compounds having a carboxyl group.

* * * * *

UNITED STATES PATENT AND TRADEMARK OFFICE
CERTIFICATE OF CORRECTION

| | |
|---|---|
| PATENT NO. | : 7,091,389 B1 |
| APPLICATION NO. | : 09/648248 |
| DATED | : August 15, 2006 |
| INVENTOR(S) | : Kato et al. |

It is certified that error appears in the above-identified patent and that said Letters Patent is hereby corrected as shown below:

<u>In Column 11</u>

At line 15, after "containing", please insert -- said--.

Signed and Sealed this

Twenty-seventh Day of March, 2007

JON W. DUDAS
*Director of the United States Patent and Trademark Office*